United States Patent [19]

Kulig et al.

[11] 4,130,158
[45] Dec. 19, 1978

[54] CENTRIFUGAL CASTING MACHINE

[75] Inventors: Frank M. Kulig, Bloomfield, Conn.; Frank H. Nealon, Plantation, Fla.

[73] Assignee: The J. M. Ney Company, Bloomfield, Conn.

[21] Appl. No.: 843,066

[22] Filed: Oct. 17, 1977

[51] Int. Cl.² .......................................... B22D 13/06
[52] U.S. Cl. .................................. 164/289; 249/137; 264/311; 425/435
[58] Field of Search ................ 425/434, 435; 264/311; 164/289; 249/137

[56] References Cited

U.S. PATENT DOCUMENTS

| | | | |
|---|---|---|---|
| 1,944,435 | 1/1934 | Kerr et al. | 164/289 X |
| 2,192,043 | 2/1940 | Hooper | 164/289 |
| 2,235,443 | 3/1941 | Steinback et al. | 164/289 |
| 2,438,817 | 3/1948 | Nalick | 164/289 X |
| 2,847,738 | 8/1958 | Lewis | 164/289 |
| 2,893,057 | 7/1959 | Rekettge | 164/289 X |
| 3,559,718 | 2/1971 | Hitchings | 164/289 X |

FOREIGN PATENT DOCUMENTS

462492  3/1951  Italy .......................................... 164/289

*Primary Examiner*—Robert L. Spicer, Jr.

[57] ABSTRACT

A centrifugal casting machine of the broken arm type has a rotatable casting arm on which a swing arm, which supports a crucible and a casting ring, is pivotably mounted. The crucible is tiltable so that upon initial rotation of the casting arm the crucible tilts to a pouring position to pour molten metal into the casting ring. A cam follower on the swing arm engages a cam on the base of the machine to hold the swing arm, during a start up period of rotation, in an orientation in which the flow path of molten metal lies in a plane approximately tangential to a circle concentric with the axis of rotation of the casting arm. This orientation and the tilting action eliminates splashing or other metal losses. After the initial period of rotation during which the metal enters the casting ring, the cam releases the swing arm for alignment with the casting arm so that the action of centrifugal force in filling the mold cavity is maximized.

17 Claims, 9 Drawing Figures

CENTRIFUGAL CASTING MACHINE

BACKGROUND OF THE INVENTION

The present invention concerns centrifugal casting machines of the broken arm type in general and casting machines employed to cast dental prostheses in particular. However, the present invention is not necessarily limited thereto and it concerns centrifugal casting machines which may be used for other purposes such as the casting of jewelry and other items.

Generally, such centrifugal casting machines include a base on which a casting arm is mounted for rotation, usually in a horizontal plane, by an electric motor or suitable other means. The so-called "broken arm" type of centrifugal casting machine has a swing arm pivotably mounted on the casting arm. The swing arm has means thereon to support a crucible and a casting ring in which a suitable mold is carried. The crucible contains a molten metal, which is usually melted in place in the crucible by a blowtorch or other means. When the metal is melted, the casting arm is then rotated, and rotation forces and the inertia of the molten metal cooperate to force the metal from the crucible into the mold. The swing arm is initially mounted at an angle to the casting arm to better align the crucible and mold during start up, and the swing arm pivots outwardly into alignment with the casting arm as the latter picks up speed.

One problem with prior art broken arm centrifugal casting machines is that upon initial rotation of the casting arm there is a tendency for the molten metal to be diverted from its true path into the mold and to splash or travel up the side walls of the crucible with attendant loss and poor casting results. Generally, it is desired that the molten metal enter the mold as quickly and completely as possible.

One prior art device which addresses this problem is shown in U.S. Pat. No. 2,297,973 entitled CENTRIFUGAL CASTING MACHINE issued on Oct. 6, 1942. This patent shows a centrifugal casting machine having a pivotable swing arm initially disposed at an acute angle to the casting arm and having a cam follower thereon. The base of the machine has a cam which engages the cam follower and is configured to accelerate outward pivoting movement of the swing arm during the start up or initial period of rotation to better align the mold with the crucible to reduce splashing of metal as the machine picks up speed. However, the teaching of this patent has a shortcoming in that as the swing arm pivots, its orientation to the path of rotation of the casting arm is constantly changing, and at a deliberately accelerated rate. Therefore, the time interval during which the swing arm might be properly oriented to the metal path of flow is actually reduced. The teaching of the patent is devoid of any recognition of the concept of orienting the swing arm to the metal flow path during start up and merely attempts to make a "running catch" of the molten metal. The difficulty is that a given cam configuration provides a given acceleration dependent upon the speed of rotation of the casting arm, and differences in metal mass and crucible configuration for different casting operations are not accounted for.

Other patents showing various casting devices are U.S. Pat. Nos. 1,466,826; 1,527,729; 2,125,080 and 2,192,043.

Another problem with prior art centrifugal casting devices is the necessity for the metal to travel up a wall of the crucible from the recessed holding portion of the crucible to its pouring lip. The molten metal must thus overcome frictional resistant forces in addition to its own inertial resistance to movement, and the likelihood of splashing or diversion of the metal from the desired true flow path into the mold is increased.

SUMMARY OF THE INVENTION

In accordance with the present invention, there is provided a centrifugal casting machine comprising a base, a casting arm mounted for rotation relative to the base, drive means to rotate the casting arm about an axis of rotation, the casting arm having a first dimension perpendicular to the axis of rotation, and a swing arm having a first dimension. Pivot means pivotally mount the swing arm on the casting arm for pivoting about an axis spaced from the axis of rotation of the casting arm. The pivot means permits pivoting of the swing arm by forces generated by rotation of the casting arm from a first position wherein the first dimension of the swing arm is angularly disposed to the first dimension of the casting arm, to a second position wherein the casting arm and the swing arm have their respective first dimensions extending in the same direction. A casting ring support is on the swing arm, and a crucible support is also on the swing arm spaced from the casting ring support along the first dimension of the swing arm. The crucible support is configured to support thereon a refractory crucible adapted to contain a molten metal and tiltable from a holding position to a pouring position by forces generated by initial rotation of the casting arm. The casting ring support and the crucible support are oriented along the first dimension of the swing arm, when it is in its said first position, so as to locate a casting ring and a crucible supported thereon in cooperative alignment to define a flow path therebetween along a line lying in a plane which is approximately tangential to a circle concentric with the axis of rotation of the casting arm, with said crucible support leading the casting ring support in the path of travel of the swing arm. When the swing arm is in its said second position, the casting ring support and the crucible support are oriented along the first dimension of the swing arm so as to locate the casting ring support radially outwardly of the crucible support relative to the casting arm axis of rotation. Guide means are operatively engaged with the swing arm to maintain the swing arm in its said first position relative to the casting arm for a limited path of movement of the casting arm about its axis of rotation, the guide means being operative to release the swing arm after its said limited path of movement to permit pivoting thereof to its said second position by forces generated by rotation of the casting arm.

Certain objects of the invention are attained when the pivot axis is disposed parallel to the axis of rotation and the guide means is adapted to maintain the swing arm in its said first position for a limited path of movement of less than one revolution of the casting arm.

Preferably, the casting arm rotates in a horizontal plane and the guide means is comprised of a cam on the base, and a cam follower on the swing arm at a location thereon spaced from the pivot means. The cam defines a cam follower path having an initial circular segment disposed concentrically about the axis of rotation and a second segment having a curvature extending oppositely to the curvature of the initial segment.

Other objects of the invention are attained by providing the casting machine in combination with a refractory crucible carried on the crucible support, the crucible having a recessed portion adapted to contain molten metal and a pouring lip disposed above the bottom of the recessed portion when the crucible is in its said holding position, the crucible further being tiltable about a tilting axis lying in a plane perpendicular to the axis of rotation of the casting arm by forces generated by initial rotation of the casting arm, from its said holding position to a pouring position oriented along the first dimension of the swing arm and in which the pouring lip is lowered relative to its location in the holding position.

The casting machine may further include alignment means biasing the swing arm toward the second position thereof.

DETAILED DESCRIPTION OF THE PREFERRED EMBODIMENTS

Figure 1:
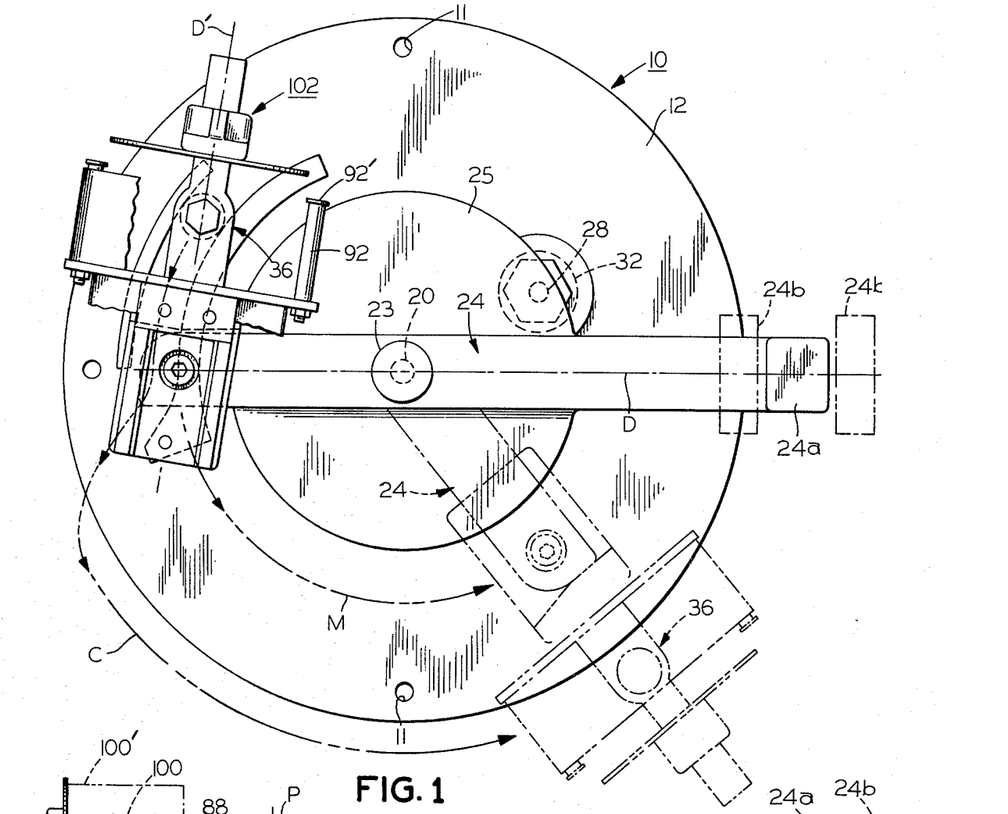
FIG. 1 is a plan view with parts broken away of one embodiment of a broken arm centrifugal casting machine in accordance with the present invention, showing the arms of the machine in solid line in their first position and in dot dash line in their second position.
Figure 2:
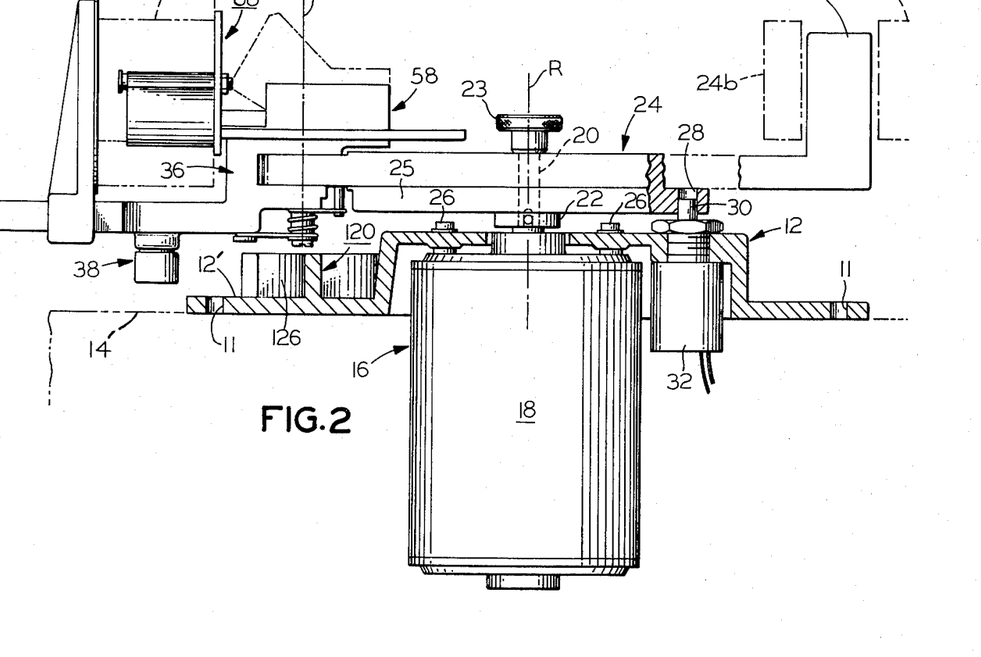
FIG. 2 is a section view in elevation of the machine of FIG. 1 showing in dot dash outline a crucible for use therewith.

Referring to FIGS. 1 and 2, a broken arm centrifugal casting machine in accordance with the invention is generally indicated at 10 and has a base 12 which is generally circular in plan view. As indicated in FIG. 2, base 12 is adapted to affix casting machine 10 in a recessed position to a support 14 shown in dot dash line. Bolt holes 11 are provided for this purpose. Obviously, base 12 could alternatively be configured to provide a portable casting machine which can be rested on any flat surface (as well as the semi-permanent recessed installation illustrated in the drawings) simply by extending base 12 generally into the configuration suggested by the dot dash lines of support 14. Support 14 may be any suitable bench or table having an opening formed therein to receive drive means 16 comprising, in the illustrated embodiment, an electric motor 18 having a drive shaft 20 projecting vertically upwardly therefrom. Drive shaft 20 has a casting arm hub 22 and a threaded lock member 23 which cooperate to secure a casting arm 24 to drive shaft 20. Casting arm 24 is keyed or otherwise suitably shaped relative to drive shaft 20 so that casting arm 24 is rotated by rotation of drive shaft 20. Shaft hub 22 is slotted, as seen in FIG. 2, to be seated upon a pin (unnumbered) projecting radially from drive shaft 20. Casting arm 24 has a discshaped plate 25 formed integrally therewith.

Mounting means comprising bolts 26 secure base 12 to the housing of electric motor 18. Casting arm 24 has a vertically extending portion 24a which provides a counterweight and is adapted to carry removable additional weights 24b shown in dot dash outline in FIGS. 1 and 2 to adjust the counterweight as required for different weights of the swing arm, as described more fully below.

At a location circumferentially offset from casting arm 24, plate 25 is provided with a recess 28 in the lowermost surface thereof which is adapted to receive a latch button 30 provided by one end of a spring loaded rod operated by solenoid 32. With latch button 30 in its illustrated extended position, it engages recess 28 and holds casting arm 24 in a fixed starting position shown by the solid line rendition of casting arm 24 in FIG. 1. Upon starting of electric motor 18, solenoid 32 operates to withdraw latch button 30 from recess 28 and free casting arm 24 for rotation.

Figures 3, 3A, 4:
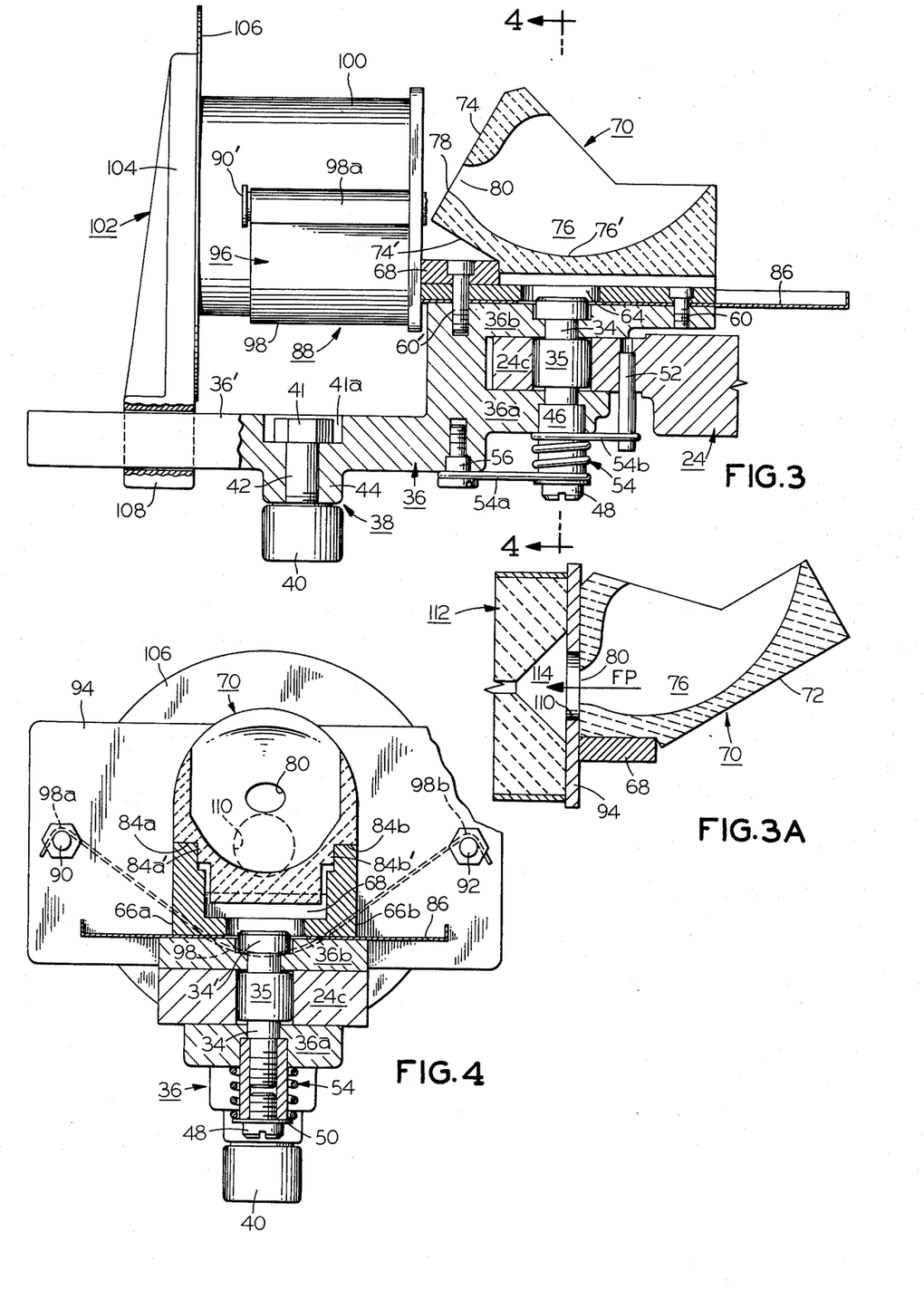
FIG. 3 is a section view in side elevation on an enlarged scale of the swing arm of the machine of FIG. 1 and showing a casting ring and a crucible supported thereon, the latter shown in section in its holding position.
FIG. 3A is a partial view of FIG. 3, showing the crucible in its pouring position.
FIG. 4 is a partial section view along line 4—4 of FIG. 3.

The end of casting arm 24 opposite that end having vertical extension 24a has a vertically extending passage (unnumbered) formed therein to receive vertically extending pivot means comprising a pivot shaft 34, as best seen in FIG. 3. Pivot shaft 34 mounts swing arm 36 on casting arm 24 for pivoting about a pivot axis (indicated by line P in FIG. 2) which is spaced from the axis of rotation R of the casting arm 24. Casting arm 24 has a first dimension D (FIG. 1) which is disposed perpendicularly to its axis of rotation R and, in the embodiment illustrated, may be described as the longitudinal axis of elongated casting arm 24. Swing arm 36 has a first dimension D' (FIG. 1) which, in the position illustrated in solid line in FIG. 1, is angularly disposed to at an acute angle first dimension D of casting arm 24. In the embodiment illustrated in FIG. 1, first dimension D' of swing arm 36 may be described on the longitudinal axis of swing arm 36. It will be noted that pivot axis P is spaced from axis of rotation R along first dimension D.

Swing arm 36 has a cam follower 38 carried thereon. As shown in FIG. 3, cam follower 38 comprises a roller 40 mounted for rotation about a roller shaft 42 which is mounted in a passageway (unnumbered) formed in a boss 44 of swing arm 36. Roller shaft 42 is provided by a bolt having a head portion 41 at one end received within a recess 41a formed in arm 36. The opposite end of shaft 42 is threaded for mounting of a bearing for roller 42 thereon.

Swing arm 36, as shown in FIG. 3, has a first portion 36' and an opposite bifurcated portion provided by forks 36a and 36b between which is received a tongue portion 24c of casting arm 24. Vertically extending passageways (unnumbered) are formed in fork portions 36a and 36b and tongue portion 24c so that pivot shaft 34 may be passed therethrough to pivotably mount swing arm 36 on casting arm 24 (FIGS. 3 and 4). Pivot shaft 34 has an upper enlarged head portion 34' which seats upon the shoulder provided by an enlarged portion of the passage in fork 36b. A roller bearing 35 is mounted upon an intermediate portion of the shaft of pivot shaft 34 and is seated within the passage formed in tongue portion 24c. Shaft 34 has threads formed on its lowermost end as shown in FIG. 4. A tubular collar 46 is threadably secured to the lower end of shaft 34 and a slot headed bolt 48 secures a washer 50 to, and encloses the lowermost end of, collar 46.

Referring again to FIG. 3, casting arm 24 has a vertically extending passage (unnumbered) formed therein in which is affixed a stud 52 which projects vertically downwardly from casting arm 24 adjacent pivot shaft 34. An alignment means comprising, in the illustrated embodiment, a torsion spring 54 is mounted over the external surface of collar 46 and retained thereon by washer 50. Torsion spring 54 has one leg thereof 54a projecting radially from the central coiled portion thereof and an opposite leg 54b similarly extending from the opposite end of the coiled portion thereof. Leg 54 is secured to swing arm 36 by means of a retaining bolt 56 and leg 54b is coiled around stud 52 to secure it thereto and thereby to casting arm 24. Torsion spring 54 has been compressed so that it is biased to further uncoil, and it thereby biases swing arm 36 towards pivoting away from its angularly disposed first position illustrated in solid line in FIG. 1 towards its second position shown in dot dash line in FIG. 1, in which first dimensions D and D' of, respectively, casting arm 24 and swing arm 36 extend in the same direction.

Figure 5:
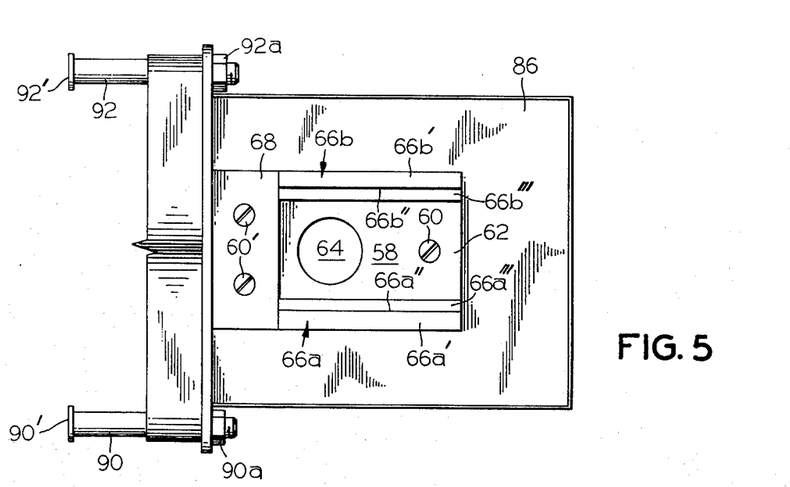
FIG. 5 is a partial plan view of the swing arm of FIG. 3 showing the crucible support platform and the frame portion of the casting ring support thereof.

Referring to FIGS. 3, 4 and 5, swing arm 36 has affixed to its bifurcated end thereof a crucible support generally indicated at 58 which is affixed to swing arm 36 atop fork 36b thereof by mounting bolts 60, 60'. Crucible support 58, as best seen in FIG. 5, generally comprises a platform 62 having a cylindrical opening 64 formed therein and a pair of spaced apart stepped side rails 66a and 66b. Crucible support 58 has a step portion 68 secured to one end thereof by mounting bolts 60'.

Figure 8:
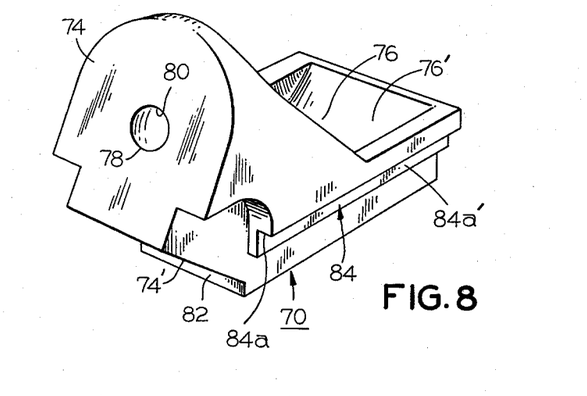
FIG. 8 is a perspective view of a crucible of the type shown in section view in FIGS. 3 and 4.

As best seen with reference to FIGS. 3 and 8, a crucible generally indicated at 70 is configured so as to rest upon crucible support 58 to be tiltably supported thereon. Crucible 70 has a first support portion 72 (FIG. 3A) and a second support portion 74, 74' (FIG. 8). Crucible 70 has a recessed portion 76 having a floor 76' adapted to contain a charge of metal. A pouring lip 78 is formed about discharge opening 80. Crucible 70 further has a shoulder portion 82 formed at an intermediate point thereof between first support portion 72 and second support portion 74. As best seen in FIGS. 4 and 8, crucible 70 has stepped undercut side portions 84 adapted to seat upon spaced apart side rails 66a and 66b.

Specifically, as seen in FIGS. 4 and 5, side rails 66a, 66b have respective horizontal top ledges 66a', 66b' (FIG. 5) connected by vertical side walls 66a'', 66b'' to recessed horizontal lips 66a''', 66b'''. As best seen in FIG. 4, undercut side portions 84 of crucible 70 have corresponding ledges 84a, 84b which rest upon ledges 66a' and 66b', respectively, and walls 84a' and 84b' which are seated against, respectively, side walls 66a'' and 66b''. As shown in FIG. 8, the ends of ledges 84a, 84b adjacent second support portion 74 are slanted upwardly so that crucible 70 is free to tilt forward to the pouring position shown in FIG. 3A under the influence of the combination of inertia and rotational forces upon start up of the rotation of casting arm 24.

Referring again to FIG. 5, a flame guard 86 is fastened to support arm 36 atop fork 36b thereof. Flame guard 86 is larger than crucible support 58, being both wider and longer than it and has a turned-up peripheral lip portion. Flame guard 86 is formed of a heat resistant material and serves to protect the remainder of the apparatus from a blowtorch or other flame applied to melt a charge of metal contained within recessed portion 76 of crucible 70.

A casting ring support generally indicated at 88 (FIGS. 1 and 3) includes a pair of spaced apart cradle support pins 90, 92 best shown in FIGS. 4 and 5. Cradle support pins 90, 92 are affixed in apertures provided in front plate 94 by means of nuts 90a, 92a received on threaded ends of pins 90, 92. As shown in FIG. 5, the ends of cradle pins 90, 92 opposite the threaded ends have enlarged stops 90'92'. Pins 90, 92 are adapted to support a casting ring cradle 96 which is provided by a strip of preformed steel or other suitable material having a bowed central portion 98 adapted to receive and support a casting ring and turned over opposite end portions 98a, 98b which are adapted to be placed over and be supported upon pins 90, 92.

FIG. 3 shows a casting ring 100 supported upon casting ring cradle 96. Casting ring 100 is of conventional design and essentially comprises a cylindrical structure within which is contained an investment mold pattern as described in more detail below with respect to FIG. 7. Casting ring 100 is normally made of metal, and for a given diameter of casting ring 100, a suitably shaped casting ring cradle 96 is provided. FIG. 2 shows in dotted outline two different sized casting rings 100, 100'.

Supported on first portion 36' of swing arm 36 is a movable casting ring stop arm generally indicated at 102. Stop arm 102 has a vertically upwardly projecting member 104 on which is carried a disc-shaped stop 106 which has a diameter larger than the largest diameter casting ring which swing arm 36 is designed to carry. A base seating portion 108 of movable stop arm 102 has a passageway formed therein whose cross section is rectangular and substantially the same as and only slightly larger than the rectangular cross section of first portion 36' of swing arm 36. Stop arm 102 is thus movable along first portion 36' of swing arm 36 so as to contact stop 106 thereof with the base of a casting ring 100. Because of the close fit of base 108 into first portion 36', any tendency of casting ring 100 to move outwardly (leftwardly as viewed in FIG. 3) will tend to tip arm 102 counterclockwise as viewed in FIG. 3 causing it to lock in place. Stop arm 102 thus serves to secure casting ring 100 in place. Obviously, means other than the close fit between first portion 36' and the passage in base part 108 of stop arm 102 could be provided to selectively lock arm 102 in place. For example, a locking screw could be threaded through base part 108 to lock it in place at a selected location along first portion 36' of swing arm 36.

Figure 7:
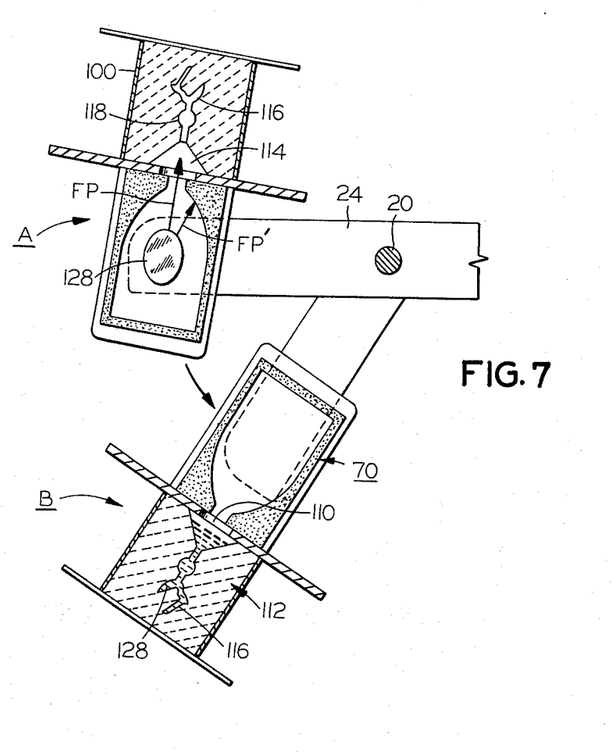
FIG. 7 is a somewhat schematic partial sectional plan view showing the swing arm of the machine of FIG. 1 sequentially in the first and second positions to illustrate the transfer of molten metal from the crucible into an investment mold carried in the casting ring.

As seen in FIGS. 3A and 4, front plate 94 has a circular opening 110 formed therein which is of larger diameter than discharge opening 80 of crucible 70 and which is aligned therewith when crucible 70 is in its pouring position. Circular opening 110 of front plate 94 is also aligned with funnel opening 114 of the investment casting mold generally indicated at 112 in FIGS. 3A and 7. As shown in FIG. 7, investment casting mold 112 comprises a suitable investment casting material within which is formed a mold cavity 116 which is connected to funnel opening 114 by a sprue 118 which has an enlarged reservoir portion formed therein and a constricted gate portion (the latter two being unnumbered) connecting to the mold cavity as is well-known in the art. The investment casting mold 112 is formed within casting ring 100 in a manner well-known in the art which forms no part of the present invention and is therefore not further described herein.

Figure 6:
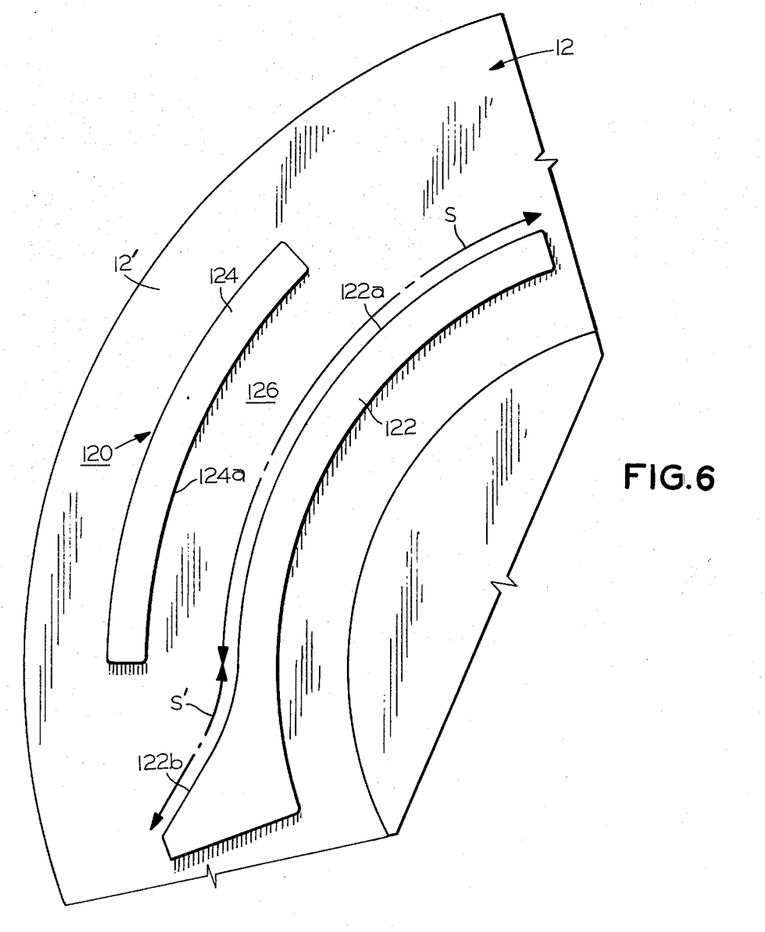
FIG. 6 is a partial plan view on an enlarged scale of the base of the machine of FIG. 1 showing the cam formed thereon.

Referring now to FIG. 6, there is shown in enlarged view a segment of base 12 on which is integrally formed a cam generally indicated at 120 comprising a pair of spaced apart land portions projecting upwardly from the top surface 12' of base 12 as best seen in FIG. 2. First land portion 122 has an initial portion defining a segment 122a of a circular wall. The extent of circular segment 122a is indicated by the dimension arrow S in FIG. 6. A second segment 122b of first land portion 122 has a curvature opposite to the curvature of segment 122a. The curvature of segment 122a is defined by a circle concentric with axis of rotation R provided by drive shaft 20. The radius of curvature of second segment 122b is opposite to that of segment 122a and moves outwardly of the circle along which segment 122a lies. Second land portion 124 of cam 120 has a circular segment 124a which lies along a segment of a circle concentric with axis of rotation R and of a larger diameter than the circle along which segment 122a lies. The result is that a circular segment of cam track 126 is formed between land portions 122 and 124. As will be noted from FIG. 1, with casting arm 24 in its starting position, roller 40 of cam follower 38 is disposed within cam track 126, the vertical surfaces of roller 40 contacting the vertical walls defining, respectively, circular segments 122a and 124a of land portions 122, 124. Although the illustrated embodiment shows land portions 122 and 124 integrally formed with base 12, obviously they may be provided by similar structure adapted to be bolted or otherwise secured in place on base 12.

Referring again to FIG. 7, the upper portion of the drawing designated A shows crucible 70 and casting ring 100 in the position they occupy relative to casting arm 24 when swing arm 36 is in its first position illustrated in solid lines in FIG. 1. A charge of molten metal 128 is contained within recessed portion 76 of crucible 70. Molten metal 128, as mentioned previously, may be melted in place within crucible 70 by a flame. Generally, it is desired by means of the centrifugal forces generated by rotation of casting arm 24 to force molten metal 128 within mold cavity 116 as quickly as possible to completely fill mold cavity 116 without voids or other irregularities. Further, it is obviously desirable to do so without splashing or losing any portion of the charge of molten metal 128 which is often a precious metal such as gold or a gold alloy.

Upon start up of rotation, the inertia of molten metal 128 permits crucible 70 to be moved by movement of casting arm 24 relative to the charge of molten metal so that funnel opening 114 moves to receive molten metal 128. In prior art devices, the pivoting action of the swing arm relative to the casting arm was relied upon in a rather hit-or-miss fashion to attempt to align funnel opening 114 properly.

In operation, prior to start up of motor 18, casting arm 24 is aligned so that latch button 30 is received within recess 28, thus positioning the components in their proper starting position with roller 40 of cam follower 38 at or near the beginning of circular segment 126 of cam 120. Upon energizing motor 18, solenoid 32 withdraws latch button 30 and shaft 20 commences to rotate casting arm 24 in a counterclockwise direction as viewed in FIG. 1.

The inertia of molten metal charge 128 causes swing arm 36 to move relative to it so that, in effect, molten metal charge 128 will describe a flow path (indicated by arrow FP in FIGS. 3A and 7) relative to support 58 (and crucible 70) into funnel opening 114. If swing arm 36 were free to pivot outwardly radially of axis of rotation R, the net result of its movement and the inertia of the molten metal would cause the molten metal to follow a flow path (indicated by arrow FP' in FIG. 7) to one side of the first dimension D' of swing arm 36, which is coincident with the center line of crucible 70 in plan view. However, roller 40 is engaged by cam 120 and constrained to initially travel along circular segment 126 of cam 120. This maintains, during an initial limited path of movement of casting arm 24, the angular alignment between swing arm 36 and casting arm 24. In other words, the angular disposition between first dimension D' of swing arm 36 and first dimension D of casting arm 24 is maintained during the limited path of movement. The effect is as if, temporarily, a third arm connected casting arm 24 to swing arm 36 at the point of connection of roller 40 thereto. During this initial limited path of movement, the crucible center line and funnel opening 114 aligned with it are held substantially in alignment with the flow path FP of molten metal charge 128. This flow path of metal is substantially a straight line lying in a plane tangential to a circle of rotation about the axis of rotation R. Sideways deviation of the flow path of molten metal charge 128 against the sides of crucible 70 which would prolong the time it takes for the molten metal to enter funnel opening 114 and possibly lead to splashing is thus avoided, and the time period required to transfer the metal charge from the crucible into funnel opening 114 is reduced as compared to that obtainable under otherwise equivalent conditions with prior art apparatus.

However, in addition to delays and possible splashing caused by sideways deviation of the metal flow path along the crucible, there is also the problem of the molten metal charge having to travel upwardly out of the recessed portion of the crucible to the pouring lip of the crucible. As will be noted in FIG. 3A, this problem is overcome by the apparatus of the present invention by the tilting feature of the crucible. Crucible 70 is configured so that forces generated by initial movement of casting arm 24 tilt the crucible into its forward position. Initial travel of molten charge 128 towards discharge opening 80 and the inertia of crucible 70 and molten metal 128 combine to tip crucible 70 into its pouring position by not later than the time at which the mass of molten metal 128 arrives at pouring lip 78 of discharge opening 80. The necessity for upward travel with resultant diminution of velocity is thus minimized and the molten metal, as may be best appreciated in FIG. 3A, travels from pouring lip 78 into funnel opening 114 in a substantially straight and nearly horizontal line. Circular opening 110 is substantially larger than discharge opening 80 so that the molten metal charge does not contact front plate 94 so as to avoid interference with its smooth transfer and possible contamination of the molten metal. Thus, molten metal charge 128 will enter funnel opening 114 substantially along the path indicated by the arrow FP in part A of FIG. 7 (and in FIG. 3A) by the time cam follower 38 reaches the end of circular segment 126 of cam 120.

The initial circular track segment 126 of cam 120 extends for only a portion of the circumference of base 12. Generally, it has been found that circular segment 126 should subtend an arc of between about 30° to 40° of rotation about axis of rotation R. In the embodiment illustrated, initial circular track segment 126 subtends an arc of about 35° of rotation. Thus, the guide means preferably is arranged to maintain swing arm 36 in its second position for between about 30° to 40° of arc of the first rotation of casting arm 24. Second segment 122b is designed to cause swing arm 36 to pivot outwardly as quickly as reasonably possible without placing undue mechanical impact and stress on the components. Advantageously, second segment 122b subtends an arc of about 20° of rotation.

It will be appreciated that this is a brief interval of time which is advantageous. In centrifugal casting processes of the type which in the apparatus of the present invention is used, metal charge 128 is normally heated to a temperature only several hundred degrees higher than its melting temperature. The heating source, usually a torch, is removed upon initiation of the rotating action. The molten metal is thus rapidly quenched by the ambient air, and the transfer from the open crucible into funnel opening 114 of the investment mold must take place as rapidly as possible and with a minimum of turbulence of splashing of the molten metal. The combination of initial rotational forces and tilting of the crucible simultaneously accomplishes this end.

However, it is also necessary that the molten metal rapidly pass through sprue 118 and into mold cavity 116. This is because the molten metal has a tendency to cool more rapidly in the small dimension areas such as the gate portion of sprue 118 and in constricted portions of mold cavity 116. To prevent premature cooling and resultant blockage, it is desirable to force the molten metal quickly and completely into all the spaces of mold cavity 116. To this end, it is desired that after the molten metal 128 has been transferred into funnel opening 114, the effect of centrifugal force in filling mold cavity 116 be maximized. Outwardly curved segment 122b of cam 120 serves to direct roller 40 of cam follower 38 rapidly radially outwardly about axis of rotation R to quickly place swing arm 36 in the second position in which casting arm 24 and swing arm 36 have their respective first dimensions D and D' extending in the same direction as shown in part B of FIG. 7. Centrifugal force, acting along a radial line from axis of rotation R, forces the molten metal into the mold cavity 116 as shown in part B of FIG. 7. In the embodiment illustrated, first dimensions D and D' are coaxially aligned with each other in the second position. Segment 122b has a radius of curvature opposite to that of 122a and accelerates the movement of swing arm 36 to its second position. This outward acceleration of swing arm 36 is abetted by torsion spring 54 which expands to bias swing arm 36 to the second position thereof once the restraint imposed by the engagement of cam follower 38 with cam 120 is terminated as casting arm 24 completes its limited path of movement along the segment of its path of rotation subtended by cam 120. Casting arm 24 then continues to rotate with swing arm 36 extended outwardly in the second position for as long as is necessary to ensure that the molten metal 128 completely fills mold cavity 116. The outward extended second position maximizes the effect of centrifugal force in forcing the molten metal into mold cavity 116. After a sufficient interval for the molten metal to solidify, usually about 1 minute for dental casting work, motor 18 is turned off and as it slows to a halt, torsion spring 54 maintains swing arm 36 in its outwardly extended second position to prevent accidental engagement of cam follower 38 with cam 120 by backpivoting of swing arm 36 as casting arm 24 slows to a halt. For dental casting work, a machine speed of about 600 RPM is appropriate.

In FIG. 1, the path of movement of cam follower 38 during the limited path of movement and an initial portion thereafter of casting arm 24 is indicated by the arrow C. The path of movement of pivot shaft 34 during the same period (and thereafter) is indicated by the arrow M in FIG. 1. After movement of swing arm 36 to its extended position, cam follower 38 rotates in a circle of rotation about drive shaft 20 which is coincident with the circular arc segment of path C and pivot shaft 34 rotates about a circle of rotation which is coincident with the circular segment of path M.

While the invention has been described in detail with respect to a particular preferred embodiment thereof, it will be apparent that upon a reading and understanding of the foregoing numerous alterations to the preferred embodiment could be employed which are nonetheless within the spirit and scope of the invention and it is intended to include such modifications within the scope of the appended claims. For example, instead of relying upon a crucible design employing an undercut portion designed to be tilted by initial rotation forces the crucible could be mounted for tilting by being provided with hubs mounted for rotation in suitable journal openings. Also a mechanical tipping device such as a spring whose operation is triggered by an inertia or solenoid switch could be utilized to obtain the desired tilting movement of the crucible. Similarly, the cam and cam follower arrangement could be replaced by other suitable guide means. For example, a spring arrangement similar to illustrated torsion spring 54 could be employed with a suitable latch mechanism which would maintain casting arm 24 and swing arm 36 in their desired angular orientation of the first position with the latch means being operable to pivot swing arm 36 to its second position after a prescribed initial period of travel.

We claim:

1. A centrifugal casting machine comprising:
   a. a base;
   b. a casting arm mounted for rotation relative to said base;
   c. drive means to rotate said casting arm about an axis of rotation, said casting arm having a first dimension perpendicular to said axis of rotation;
   d. a swing arm having a first dimension;
   e. pivot means pivotally mounting said swing arm on said casting arm for pivoting about an axis spaced from said axis of rotation of said casting arm, said pivot means permitting pivoting of said swing arm by forces generated by rotation of said casting arm from a first position wherein said first dimension of said swing arm is angularly disposed to said first dimension of said casting arm, to a second position wherein said casting arm and said swing arm have their respective first dimensions extending in the same direction;
   f. a casting ring support on said swing arm;
   g. a crucible support on said swing arm spaced from said casting ring support along said first dimension of said swing arm, said crucible support being configured to support thereon a refractory crucible adapted to contain a molten metal and tiltable from a holding position to a pouring position by forces generated by initial rotation of said casting arm, said casting ring support and crucible support being oriented along said first dimension of said swing arm: (i) in said first position thereof, to locate a casting ring and a crucible supported thereon in cooperative alignment to define a flow path therebetween along a line lying in a plane which is approximately tangential to a circle concentric with said axis of rotation of said casting arm, with said crucible support leading said casting ring support in the path of travel of said swing arm and, (ii) in said second position thereof, to locate said casting ring support radially outwardly of said crucible support relative to said casting arm axis of rotation; and h. guide means operatively engaged with said swing arm to maintain said swing arm in said first position relative to said casting arm for a limited path of movement of said casting arm about its axis of rotation, said guide means being operative to release said swing arm after said limited path of movement to permit pivoting thereof to said second position by forces generated by rotation of said casting arm.

2. The casting machine of claim 1 wherein said pivot axis is disposed parallel to said axis of rotation and said guide means is adapted to maintain said swing arm in said first position for a limited path of movement of less than one revolution of said casting arm.

3. The casting machine of claim 2 wherein said casting arm rotates in a horizontal plane.

4. The casting machine of claim 2 wherein said guide means is comprised of:
  (i) a cam on said base, and
  (ii) a cam follower on said swing arm at a location thereon spaced from said pivot means;
said cam defining a cam follower path having an initial circular segment disposed concentrically about said axis of rotation and a second segment having a curvature extending oppositely to the curvature of said initial segment.

5. The casting machine of claim 4 wherein said initial circular segment of said cam subtends an arc of about 30° to 40° about said axis of rotation.

6. The casting machine of claim 4 wherein said initial circular segment subtends an arc of about 35° about said axis of rotation.

7. The casting machine of claim 4 wherein said second segment subtends an arc of about 20° about said axis of rotation.

8. The casting machine of claim 4 wherein said cam follower comprises a roller mounted on said swing arm and extending therebelow and said cam comprises a track having at least one wall defining said cam follower path and adapted to engage said roller.

9. The casting machine of claim 8 wherein said roller is mounted for rotation about a roller axis parallel to said axis of rotation.

10. The casting machine of claim 1 wherein said crucible support includes side rails adapted to engage and retain thereon a refractory crucible.

11. The casting machine of claim 1 further including alignment means biasing said swing arm toward said second position thereof.

12. The casting machine of claim 11 wherein said alignment means comprises a torsion spring having a first leg operatively associated with said swing arm and a second leg operatively associated with said casting arm.

13. The casting machine of claim 1 in combination with a refractory crucible carried on said crucible support, said crucible having a recessed portion adapted to contain molten metal and a pouring lip disposed above the bottom of said recessed portion when said crucible is in said holding position, said crucible further being tiltable about a tilting axis lying in a plane perpendicular to said axis of rotation of said casting arm by forces generated by initial rotation of said casting arm, from said holding position to a pouring position oriented along said first dimension of said swing arm and in which said pouring lip is lowered relative to its location in said holding position.

14. The casting machine of claim 13 wherein said crucible is configured to rest upon a first support portion thereof in its said holding position, and to rest upon a second support portion thereof in its said pouring position.

15. The casting machine of claim 14 wherein said crucible support has a step portion having a face thereof extending perpendicularly of said first dimension of said swing arm and said crucible has a shoulder portion adapted to engage said face of said step portion for tilting of said crucible about said step portion.

16. The casting machine of claim 1 wherein said crucible support comprises a face plate having support means thereon and a pour opening formed therein and aligned with said first dimension of said swing arm, and a movable stop assembly spaced along said first dimension of said swing arm from said face plate, said crucible support being adapted to support a casting ring on said support means between said face plate and said stop assembly.

17. A centrifugal casting machine comprising:
  a. a base;
  b. a casting arm mounted for rotation relative to said base;
  c. drive means to rotate said casting arm in a horizontal plane about a vertical axis of rotation, said casting arm having longitudinal axis extending perpendicularly to said axis of rotation;
  d. a swing arm having a first dimension;
  e. pivot means pivotally mounting said swing arm on said casting arm for pivoting about a pivot axis parallel to and spaced from said axis of rotation of said casting arm, said pivot means permitting pivoting of said swing arm by forces generated by rotation of said casting arm from a first position wherein said first dimension of said swing arm is angularly disposed to said longitudinal axis of said casting arm, to a second position wherein said casting arm longitudinal axis and said swing arm first dimension extend in the same direction;
  f. a casting ring support frame on said swing arm;
  g. a crucible support on said swing arm spaced from said casting ring support along said first dimension of said swing arm, said crucible support comprising a platform having means to tiltably support thereon a refractory crucible adapted to contain a molten metal and tiltable from a holding position to a pouring position by forces generated by initial rotation of said casting arm, said casting ring support and crucible support being oriented along said first dimension of said swing arm: (i) in said first position thereof, to locate a casting ring and a crucible supported thereon in cooperative alignment to define a flow path therebetween along a line lying in a plane which is approximately tangential to a circle concentric with said axis of rotation of said casting arm, with said crucible support leading said casting ring support in the path of travel of said swing arm and, (ii) in said second position thereof, to locate said casting ring support outwardly of said crucible support relative to said casting arm axis of rotation;

h. cam follower means on said swing arm spaced from said pivot means along said first dimension of said swing arm; and i. cam means on said base adapted to engage said cam follower means to maintain said swing arm in said first position for less than one revolution of said casting arm about its axis of rotation, and to release said cam follower prior to said one revolution of said casting arm to permit pivoting thereof to said second position by forces generated by rotation of said casting arm.

* * * * *